US008778687B2

(12) United States Patent
Levine et al.

(10) Patent No.: US 8,778,687 B2
(45) Date of Patent: *Jul. 15, 2014

(54) METHOD AND APPARATUS FOR DETERMINING THE HEMATOCRIT OF A BLOOD SAMPLE UTILIZING THE INTRINSIC PIGMENTATION OF HEMOGLOBIN CONTAINED WITHIN THE RED BLOOD CELLS

(71) Applicant: Abbott Point of Care, Inc., Princeton, NJ (US)

(72) Inventors: Robert A. Levine, Guilford, CT (US); Stephen C. Wardlaw, Lyme, CT (US); Darryn Unfricht, North Haven, CT (US); Niten V. Lalpuria, Mumbai (IN)

(73) Assignee: Abbott Point of Care, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/751,938

(22) Filed: Jan. 28, 2013

(65) Prior Publication Data

US 2013/0208972 A1    Aug. 15, 2013

Related U.S. Application Data

(63) Continuation of application No. 13/418,007, filed on Mar. 12, 2012, now Pat. No. 8,361,799, which is a continuation of application No. 13/116,837, filed on May 26, 2011, now Pat. No. 8,133,738, which is a continuation of application No. 12/408,256, filed on Mar. 20, 2009, now Pat. No. 7,951,599.

(60) Provisional application No. 61/038,557, filed on Mar. 21, 2008, provisional application No. 61/038,574, filed on Mar. 21, 2008.

(51) Int. Cl.
*G01N 33/48*     (2006.01)
*G01N 33/86*     (2006.01)
*G01N 33/72*     (2006.01)
*G01N 33/80*     (2006.01)
*G01N 15/14*     (2006.01)

(52) U.S. Cl.
CPC ............. *G01N 33/80* (2013.01); *G01N 33/48* (2013.01); *G01N 33/721* (2013.01); *G01N 33/86* (2013.01); *G01N 15/1463* (2013.01); *G01N 15/1475* (2013.01)

USPC .......... 436/70; 436/63; 436/66; 436/164; 436/165; 422/73; 422/82.05; 422/82.09; 600/368; 382/134; 356/39

(58) Field of Classification Search
CPC ... G01N 33/48; G01N 33/49; G01N 33/4905; G01N 33/491; G01N 33/72; G01N 33/721; G01N 33/80; G01N 33/86; G01N 21/03; G01N 15/1463; G01N 15/1475; G01N 2015/0073; A61B 5/145; A61B 5/14535
USPC ......... 436/63, 66, 70, 164, 165; 422/68.1, 73, 422/82.05, 82.09; 435/2; 600/322, 368; 382/128, 133, 134; 356/30, 40, 39
See application file for complete search history.

(56) References Cited

U.S. PATENT DOCUMENTS 4,023,716 A    5/1977    Shapiro
4,197,088 A    4/1980    Meserol et al.
(Continued)

FOREIGN PATENT DOCUMENTS

DE    10011235    9/2001
DE    10240742    3/2004
(Continued)

OTHER PUBLICATIONS

Sun et al, "Microminiaturized immunoassays using quantum dots as fluorescent label by laser confocal scanning fluorescence detection," Journal of Immunological Methods, Elsevier Science Publishers, vol. 249, No. 1-2, pp. 85-89, Mar. 2001.
(Continued)

*Primary Examiner* — Maureen Wallenhorst
(74) *Attorney, Agent, or Firm* — O'Shea Getz P.C.

(57) ABSTRACT

A method and apparatus for determining the hematocrit of a blood sample disposed within an analysis chamber, the method including the steps of: a) imaging at least a portion of the sample that contains one or more red blood cells and one or more areas void of red blood cells; b) determining a representative optical density value for a plurality of image units optically aligned with portions of the red blood cells, and assigning an optical density first boundary value to those image units; c) determining a representative optical density value of a plurality of image units optically aligned with the one or more regions of the sample devoid of red blood cells, and assigning a second optical density boundary value to those image units; and d) determining the hematocrit of the sample.

3 Claims, 5 Drawing Sheets

(56) References Cited

U.S. PATENT DOCUMENTS

| | | | |
|---|---|---|---|
| 4,487,081 A | 12/1984 | De Vaughn et al. | |
| 4,615,878 A | 10/1986 | Kass | |
| 5,012,818 A | 5/1991 | Joishy | |
| 5,068,181 A | 11/1991 | Driscoll | |
| 5,192,511 A | 3/1993 | Roach | |
| 5,284,771 A | 2/1994 | Fan et al. | |
| 5,447,838 A | 9/1995 | Meiklejohn et al. | |
| 5,454,268 A | 10/1995 | Kim | |
| 5,460,782 A | 10/1995 | Coleman et al. | |
| 5,739,042 A | 4/1998 | Frengen | |
| 5,768,407 A | 6/1998 | Shen et al. | |
| 5,770,160 A | 6/1998 | Smith et al. | |
| 5,851,835 A | 12/1998 | Groner | |
| 5,948,686 A * | 9/1999 | Wardlaw | 436/63 |
| 6,127,184 A | 10/2000 | Wardlaw | |
| 6,235,536 B1 * | 5/2001 | Wardlaw | 436/172 |
| 6,544,793 B2 | 4/2003 | Berndt | |
| 6,723,290 B1 | 4/2004 | Wardlaw | |
| 6,730,521 B1 | 5/2004 | Cassells | |
| 6,819,408 B1 | 11/2004 | Scrivens | |
| 6,866,823 B2 | 3/2005 | Wardlaw | |
| 6,929,953 B1 | 8/2005 | Wardlaw | |
| 7,731,901 B2 * | 6/2010 | Wardlaw | 422/73 |
| 7,850,916 B2 | 12/2010 | Wardlaw | |
| 7,903,241 B2 * | 3/2011 | Wardlaw et al. | 356/39 |
| 7,912,534 B2 | 3/2011 | Grinvald | |
| 7,929,121 B2 * | 4/2011 | Wardlaw et al. | 356/39 |
| 7,929,122 B2 * | 4/2011 | Wardlaw et al. | 356/40 |
| 7,951,599 B2 * | 5/2011 | Levine et al. | 436/70 |
| 8,081,303 B2 | 12/2011 | Levine | |
| 8,133,738 B2 * | 3/2012 | Levine et al. | 436/70 |
| 8,310,658 B2 | 11/2012 | Wardlaw | |
| 8,361,799 B2 * | 1/2013 | Levine et al. | 436/70 |
| 2002/0028158 A1 | 3/2002 | Wardlaw | |
| 2002/0131902 A1 | 9/2002 | Levy | |
| 2003/0025896 A1 | 2/2003 | Oever et al. | |
| 2003/0224534 A1 | 12/2003 | Kawate | |
| 2004/0048330 A1 | 3/2004 | Bittner | |
| 2004/0165090 A1 | 8/2004 | Ning | |
| 2005/0002826 A1 | 1/2005 | Oguni et al. | |
| 2005/0026197 A1 | 2/2005 | Dertinger | |
| 2005/0277159 A1 | 12/2005 | Lehmann et al. | |
| 2006/0159962 A1 | 7/2006 | Chandler et al. | |
| 2006/0258018 A1 | 11/2006 | Curl et al. | |
| 2007/0087442 A1 | 4/2007 | Wardlaw | |
| 2007/0243117 A1 | 10/2007 | Wardlaw | |
| 2008/0070317 A1 | 3/2008 | Bradshaw et al. | |
| 2009/0238438 A1 * | 9/2009 | Wardlaw et al. | 382/134 |
| 2009/0238439 A1 * | 9/2009 | Wardlaw et al. | 382/134 |
| 2009/0239257 A1 * | 9/2009 | Levine et al. | 435/34 |
| 2010/0015691 A1 | 1/2010 | Krogh | |
| 2011/0149061 A1 * | 6/2011 | Wardlaw et al. | 348/77 |
| 2011/0164803 A1 * | 7/2011 | Wang et al. | 382/134 |

FOREIGN PATENT DOCUMENTS

| | | |
|---|---|---|
| EP | 0366151 | 5/1990 |
| EP | 0642829 | 3/1995 |
| EP | 1239284 | 9/2002 |
| GB | 2254414 | 10/1992 |
| JP | 6308119 | 11/1994 |
| WO | 9802727 | 1/1998 |
| WO | 0057891 | 5/2000 |
| WO | 0223154 | 3/2002 |

OTHER PUBLICATIONS

Goldman et al., "Multiplexed Toxin Analysis using Four Colors of Quantum Dot Fluororeagents," Analytical Chemistry, American Chemical Society, vol. 76, No. 3, pp. 684-688, Feb. 2004.

Matzdorff et al., "Quantitative assessment of platelets, platelet microparticles, and platelet aggregates in flow cytometry," The Journal of Laboratory and Clinical Medicine, vol. 131, No. 6, pp. 507-517, Jun. 1998.

Hu Hu et al, "Effects of insulin on platelet and leukocyte activity in whole blood," Thrombosis Research, vol. 107, No. 5, pp. 209-215, Sep. 2002.

Sbrana et al., "Relationships between optical aggregometry (type born) and flow cytometry in evaluating ADP-induced platelet activation," Cytometry, Part B, Clinical Cytometry, vol. 74, No. 1, pp. 30-39, Jan. 2008.

Fishbane et al., "Reticulocyte hemoglobin content in the evaluation of iron status of hemodialysis patients", Kidney International, vol. 52, pp. 217-222, 1997.

Wray et al. "Characterization of the Near Infrared Absorption Spectra of Cytochrome aa3 and Haemoglobin for the Non-Invasive Monitoring of Cerebral Oxygenation", Biochimica et Ciophysica Acta, 933 (1988), 184-192.

Kim et al. "Engineering in Medicine and Biology: Extinction Coefficients of Hemoglobin for Near-Infrared Spectroscopy of Tissue", Mar./Apr. 2005.

Hematocrit/HCT and Calulated Hemoglobin/HB, Article 714178-00H, Rev. Date: Jun. 11, 2008.

Wood et al., "Resonance Raman Spectroscopy of Red Blood Cells Using Near-Infrared Laser Excitation", Analytical and Bioanalytical Chemistry, vol. 387, No. 5, Dec. 7, 2006, pp. 1691-1703.

Ellis et al., "Applicaton of Image Analysis for Evaluation of Red Blood Cell Dynamics in Capillaries", Microvascular Research, vol. 44, No. 2, Sep. 1, 1992, pp. 214-225.

Wan et al., "Contact Mechanics of a Thin-Walled Capsule adhered onto a Rigid planar Substrate", Medical & Biological Engineering & Computing 2001, vol. 39, p. 605-608.

Pfeifer, "Solder Bump Size and Shape Modeling and Experimental Validation", IEEE, 1997, 452-457.

* cited by examiner

METHOD AND APPARATUS FOR DETERMINING THE HEMATOCRIT OF A BLOOD SAMPLE UTILIZING THE INTRINSIC PIGMENTATION OF HEMOGLOBIN CONTAINED WITHIN THE RED BLOOD CELLS

The present application is a continuation of U.S. patent application Ser. No. 13/418,007 filed Mar. 12, 2012, now issued as U.S. Pat. No. 8,361,799, which is a continuation of U.S. patent application Ser. No. 13/116,837, filed on May 26, 2011, now issued as U.S. Pat. No. 8,133,738, which is a continuation of U.S. patent application Ser. No. 12/408,256, filed on Mar. 20, 2009, now issued as U.S. Pat. No. 7,951,599, which claims priority to U.S. Provisional Patent Application Ser. Nos. 61/038,557, filed Mar. 21, 2008, and 61/038,574, filed Mar. 21, 2008.

BACKGROUND OF THE INVENTION

1. Technical Field

The present invention relates to apparatus and methods for analysis of blood samples in general, and for the determination of the hematocrit of a blood sample in particular.

2. Background Information

Physicians, veterinarians and scientists have examined human and animals' biologic fluids, especially blood, in order to determine constituent particulate quantities as well as to identify the presence of unusual particulates not seen in healthy subjects. The particulates generally measured, quantified and identified include red blood cells (RBCs), white blood cells (WBCs), and platelets. RBC analyses can include determinations of RBC number, size, volume, shape, hemoglobin content and concentration, and the hematocrit (also referred to as the packed cell volume). RBC analyses can also involve determining the presence and/or concentration of certain components within the red blood cells such as DNA, RNA, including the detection of the presence and/or enumeration of hematoparasites (e.g., malarial parasites) either in the RBCs or trypanosomes which are extracellular or leishmaniasis organisms which are in the WBCs as well as many other hematoparasites. WBC analyses can include a determination of the population frequency of WBC sub types generally referred to as a differential WBC count, as well as the notification of any unusual cell types not found in healthy subjects. Platelet (or in certain animals including birds, reptiles and fish, thrombocytes which are similar in function to platelets in mammals but are about ten times larger and nucleated) analyses can include platelet number, size, shape texture, and volume determinations, including determining the presence of clumps of platelets or thrombocytes within the sample.

Known blood examination techniques, described in detail medical texts such as Wintrobe's Clinical Hematology 12th Edition, generally divides the examination methods into manual, centrifugal, and impedance type methods. Manual methods for cell enumeration typically involve the creation of an accurately determined volume of a blood or fluid sample that is quantitatively diluted and visually counted in a counting chamber. Manual examination methods include examining a peripheral smear where the relative amounts of the particulate types are determined by visual inspection. Centrifugal examination methods involve centrifuging the sample, causing the sample to separate into constituent layers according to the relative densities of the constituents. Each component layer can be stained to enhance visibility or detection. Impedance methods involve the examination of an accurate amount of blood which is treated according to the particulate being measured; e.g., lysing RBCs for enumeration of the nucleated cells and volumetrically diluting the sample in a conductive fluid. The process typically involves monitoring a current or voltage applied to sample passing through a narrow passage to determine the effect particles have on the current/voltage as the particles pass through in single file. Other techniques involve analyzing the intensity and angle of scatter of light incident to particulates passing single file through a light beam. Flow cytometric methods can also be used that involve staining particulates of interest in suspension with fluorophores, exciting the stained particulates with light of appropriate wavelengths, and analyzing the emission of the individual particulates/cells.

All of the aforementioned methods, other than the peripheral smear or centrifugal separation, require dispensing a precise volume of sample. Inaccuracies in the sample volume will result in quantitative errors of the same magnitude in the associated analysis. With the exception of centrifugal methods, all of the aforementioned methods also require the sample to be mixed with one or more liquid reagents or diluents, and also require calibration of the instrument to obtain accurate results. In the case of peripheral smears, a high degree of training is needed to properly examine the smear. A number of the aforementioned methods generate large volumes of contaminated waste which is expensive to handle. Additionally, the above-described methods are not suitable to determine the complete blood count (CBC) in birds, reptiles, fish and certain mammals where the red blood cells size is very small.

Despite the complex amount of hematologic information obtained from the complete blood count, one test is most often needed: the hematocrit. It is the hematocrit that tells the physician whether the patient is anemic due to bleeding or nutritional causes such as the relatively common iron deficiency in growing children and women of reproductive age, associated disease processes such as chronic infections, metabolic disease such as uremia or neoplastic illnesses as well as pharmacologic effects. An elevated hematocrit indicates the presence of too many red blood cells due to disease processes such as dehydration where the blood is concentrated. An elevated hematocrit can also be indicative of true increases in red blood cell mass that occur as a result of disease processes such as polycythemia, or pharmacologic effects such as the administration of too much anabolic steroids or chronic hypoxia due to lung disease or certain types of congenital heart disease. The importance and utility of the hematocrit make it one of the most frequently requested tests performed on blood. Consequently, easy, accurate, inexpensive and rapidly available hematocrit determinations are highly desirable and will benefit patients. An instrument that can use a disposable analysis chamber, one that can operate with no internal fluidics other than capillary flow (i.e., one that is operable independent of gravity and orientation), and one that can be utilized as a handheld device would be a great benefit.

SUMMARY OF THE INVENTION

According to an aspect of the present invention, a method for determining the hematocrit of a blood sample is provided. The method includes the steps of: 1) providing a substantially undiluted blood sample; 2) depositing the sample into an analysis chamber adapted to quiescently hold the sample for analysis, the chamber defined by an interior surface of a first panel, and an interior surface of a second panel, wherein both panels are transparent, and the chamber has a height extending between the interior surfaces of the panels, which height is such that at least some of the RBCs within the sample, either individually or in aggregate, contact both of the interior surfaces of the panels and one or more RBC void areas within the quiescent sample extend between the interior surfaces; 3) imaging at least a portion of the quiescent sample, which sample portion contains the RBCs and one or more RBC void areas contacting the interior surfaces, to determine an optical density of the imaged portion of the sample on a per unit basis; 4) selecting and averaging the optical density values of the image units aligned with some of the individual RBCs or RBC aggregates contacting both the interior surfaces, and assigning an upper boundary value of 100% to the average optical density value of those image units; 5) selecting the optical density values of the image units aligned with the one or more RBC void areas, and assigning a lower boundary value of 0% to the optical density values of those image units; and 6) determining the hematocrit of the sample by assigning relative values to the optical density value of each image unit of the imaged sample contained in the chamber portion as a function of the upper and lower boundary values, and averaging the relative values.

According to another aspect of the invention, an apparatus for determining the hematocrit of a substantially undiluted blood sample quiescently residing within an analysis chamber is provided. The chamber is defined by a pair of transparent panels, and has a height extending between interior surfaces of the panels. The chamber height is such that at least some RBCs within the sample individually or in aggregate contact both of the interior surfaces and one or more areas void of RBCs within the quiescent sample extend between the interior surfaces. The apparatus includes an imaging unit and a programmable analyzer. The imaging unit includes an illuminator and an image dissector, and is operable to image at least a portion of a sample quiescently residing within the chamber that contains the RBCs or RBC aggregates and the one or more RBC void areas contacting the interior surfaces, and produce image signals representative of such imaged sample portion. The programmable analyzer is adapted to determine, using the image signals, optical density values of the imaged portion of the sample on a per image unit basis. The analyzer is further adapted to select and average the optical density values of the image units optically aligned with the at least some RBCs and/or RBC aggregates contacting the interior surfaces, and assign an upper boundary value of 100% to the average optical density value of those image units. The analyzer is further adapted to select the optical density values of the image units optically aligned with the one or more RBC void areas and assigning a lower boundary value of 0% to the optical density values of those image units, and to determine the hematocrit of the sample by assigning relative values to the optical density value of each image unit of the imaged sample portion as a function of the upper and lower boundary values, and averaging the relative values.

An advantage of the present invention is that it can be used to determine a hematocrit value using an extremely small sample volume that may be obtained directly from the patient by capillary puncture rendering it more useful for point of care application or from a venous sample if desired.

Another advantage of the present invention is that a hematocrit value can be determined independent of knowledge of the magnification factor of the instrument (size of image/image unit) and without knowledge of the height of the chamber. Consequently, the present method has great versatility regarding the type of analysis instrument and chamber that can be used.

Another advantage of the present invention it is operable to determine the hematocrit of a blood sample using only the intrinsic pigmentation of hemoglobin, and therefore does not need the addition of any dyes or stains. The high molar extinction coefficient of hemoglobin at several different wavelengths permits determinations of its relative or absolute concentration within very small light path distances, as small as a few microns.

Another advantage of the present method is that it operates free of external and internal fluidics, and independent of gravity or orientation, and therefore is adaptable for use in a hand held device.

The present method and advantages associated therewith will become more readily apparent in view of the detailed description provided below, including the accompanying drawings.

DETAILED DESCRIPTION OF EMBODIMENTS OF THE INVENTION

The present method and apparatus for determining the hematocrit of a blood sample allows the hematocrit to be determined without the adding dyes, reagents (other than anticoagulants in some embodiments) or diluents to the sample, or the need to precisely know the volume of the sample or the height or volume of the analysis chamber. In some embodiments, the present method and apparatus includes the addition of an agent which causes the aggregation of the RBCs. Agents such as polybrene, anti-glycophorin antibody, or the like cause almost instant aggregation of RBCs within the sample. At least some of those RBC aggregates will be in contact with the opposing interior surfaces of the chamber. The optical density of an RBC aggregate extending between the surfaces can be used in the same manner as the optical density for a single cell in calculating the hematocrit.

The present method utilizes an analysis chamber that is operable to quiescently hold a sample of substantially undiluted whole blood for analysis. The chamber is typically sized to hold about 0.2 to 1.0 µl of sample, but the chamber is not limited to any particular volume capacity, and the capacity can vary to suit the analysis application. The phrase "substantially undiluted" as used herein describes a blood sample which is either not diluted at all or has not been diluted purposefully, but has had some reagents added thereto for purposes of the analysis. To the extent the addition of the reagents dilutes the sample, if at all, such dilution has no clinically significant impact on the analysis performed. Typically, the only reagents that will be used in performing the present method are anticoagulants (e.g., EDTA, heparin) and in some instances an isovolumetric sphering agent, or an aggregating agent and these are not intended to dilute the sample. Under certain circumstances (e.g., very rapid analysis), it may not be necessary to add the anticoagulating agent, but it is preferable to do so in most cases to ensure the sample is in a form acceptable for analysis. The term "quiescent" is used to describe that the sample is deposited within the chamber for analysis, and the sample is not purposefully moved relative to the chamber during the analysis; i.e., the sample resides quiescently within the chamber. To the extent that motion is present within the blood sample, it will predominantly be that due to Brownian motion of the blood sample's formed constituents, which motion is not disabling of the use of the device of this invention.

Figure 1:
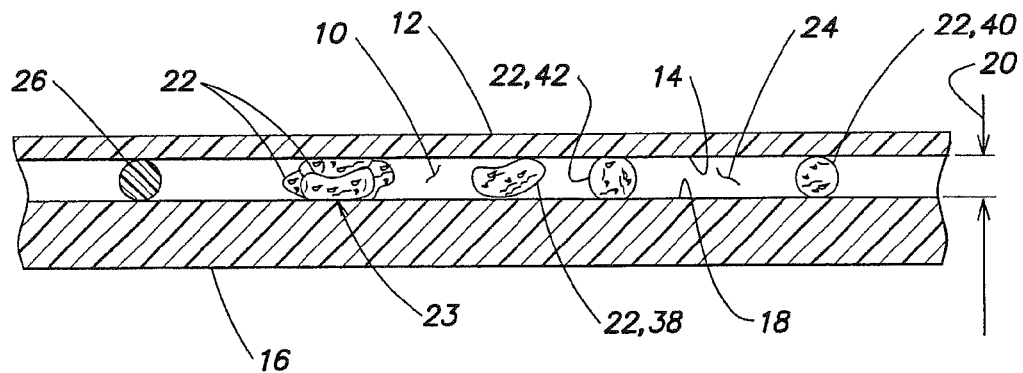
FIGS. 1-4 are cross-sectional diagrammatic representations of analysis chambers that may be used in the present method.
Figure 2:
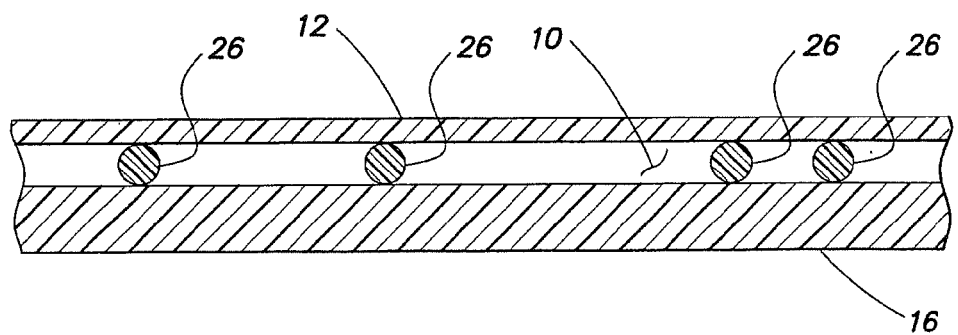

Now referring to FIG. 1, the analysis chamber 10 is defined by a first panel 12 having an interior surface 14, and a second panel 16 having an interior surface 18. The panels 12, 16 are both sufficiently transparent to allow the transmission of light along predetermined wavelengths there through in an amount sufficient to perform the optical density analysis described below. At least a portion of the panels 12, 16 are parallel with one another, and within that portion the interior surfaces 14, 18 are separated from one another by a height 20 such that at least some individual RBCs 22 within a sample each individually contact both interior surfaces 14, 18, and/or one or more aggregates 23 of RBCs within the sample each contact both interior surfaces 14, 18 of the chamber panels 12, 16, and one or more RBC void areas (e.g., lacunae) 24 within the quiescent sample extend between the interior surfaces, as will be discussed in greater detail below. The present method can utilize a variety of different analysis chambers types having the aforesaid characteristics, and is not therefore limited to any particular type of analysis chamber. An analysis chamber having parallel panels 12, 16 simplifies the analysis and is therefore preferred, but is not required for the present invention; e.g., a chamber having one panel disposed at a known non-parallel angle relative to the other panel could be used.

Now referring to FIGS. 2-5, an example of an acceptable chamber 10 is shown that includes a first panel 12, a second panel 16, and at least three separators 26 disposed between the panels 12, 16. The separators 26 can be any structure that is disposable between the panels 12, 16, operable to space the panels 12, 16 apart from one another. The dimension 28 of a separator 26 that extends between the panels 12, 16 is referred to herein as the height 28 of the separator 26. The heights 28 of the separators 26 typically do not equal one another exactly (e.g., manufacturing tolerances), but are within commercially acceptable tolerance for spacing means used in similar analysis apparatus. Spherical beads are an example of an acceptable separator 26 and are commercially available from, for example, Bangs Laboratories of Fishers, Ind., U.S.A.

Figure 3:
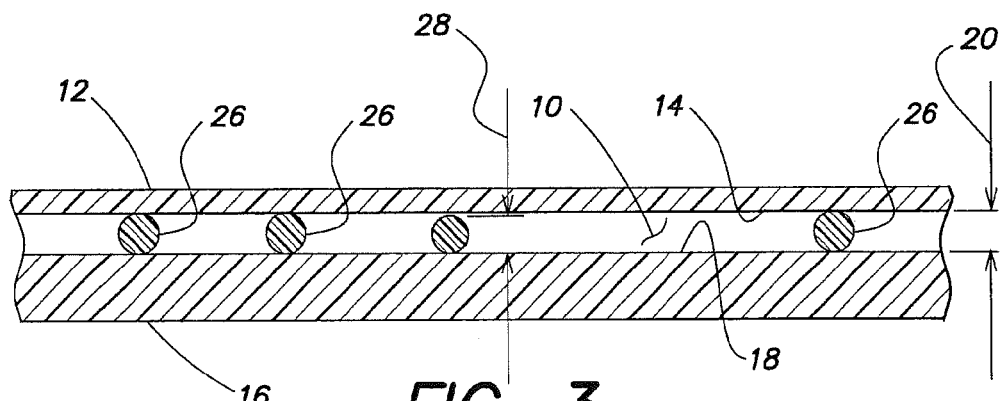
Figure 4:
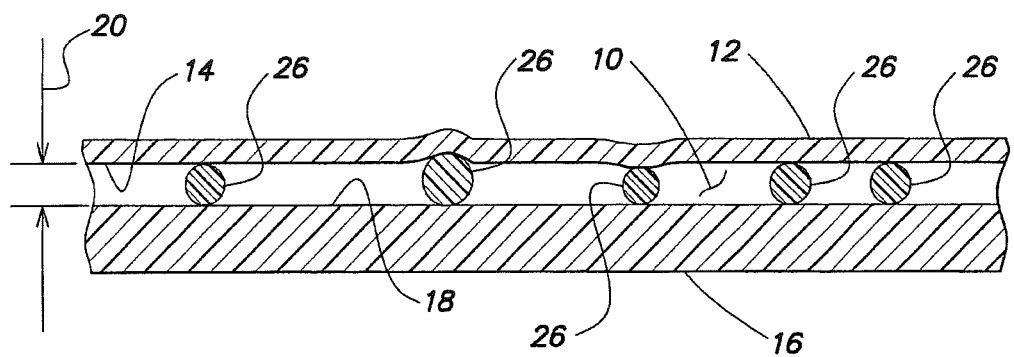
Figure 5:
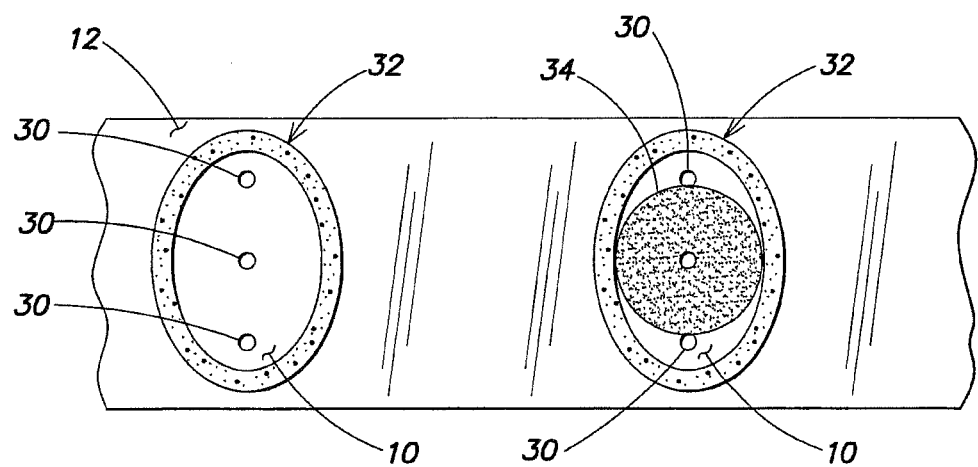
FIG. 5 is a diagrammatic planar view of a tape having a plurality of analysis chambers.

In the chamber embodiment shown in FIG. 3, the separators 26 consist of a material that has greater flexibility than one or both of the first panel 12 and the second panel 16. As can be seen in FIG. 3, the larger separators 26 are compressed to the point where most separators 26 are touching the interior surfaces of the panels 12, 16, thereby making the chamber height just slightly less than the mean separator 26 diameters. In the chamber embodiment shown in FIG. 4, the separators 26 consist of a material that has less flexibility than one or both of the first panel 12 and the second panel 16. In FIG. 4, the first panel 12 is formed from a material more flexible than the spherical separators 26 and the second panel 16, and will overlay the separators 26 in a tent-like fashion. In this embodiment, although small local regions of the chamber 10 may deviate from the desired chamber height 20, the average height 20 of the chamber 10 will be very close to that of the mean separator 26 diameter. Analysis indicates that the mean chamber height 20 can be controlled to one percent (1%) or better at chamber heights of less than four microns using this embodiment. Subject to the flexibility characteristics described above (as well as other factors such as the distribution density of the separators), the separators 26 and panels 12, 16 can be made from a variety of materials, provided the panels 12, 16 are sufficiently transparent. Transparent plastic films consisting of acrylic or polystyrene are examples of acceptable panels 12, 16, and spherical beads made of polystyrene, polycarbonate, silicone, and the like, are acceptable separators 26. A specific example of an acceptable separator is spheres made of polystyrene that are commercially available, for example, from Thermo Scientific of Fremont, Calif., U.S.A., catalogue no. 4204A, in four micron (4 μm) diameter. Referring to FIG. 5, the panel 12 that is to be vertically disposed above the other includes a plurality of ports 30 disposed at regular intervals (e.g., that act as air vents), and the panels 12, 16 are bonded together at points. In some embodiments, the bonding material 32 forms an outer chamber wall operable to laterally contain the sample 34 within the analysis chamber 10. This example of an acceptable analysis chamber is described in greater detail in U.S. Patent Application Publication Nos. 2007/0243117, 2007/0087442, and U.S. Provisional Patent Application Nos. 61/041,783, filed Apr. 2, 2008; and 61/110,341, filed Oct. 31, 2008, all of which are hereby incorporated by reference in their entirety.

Figure 6:
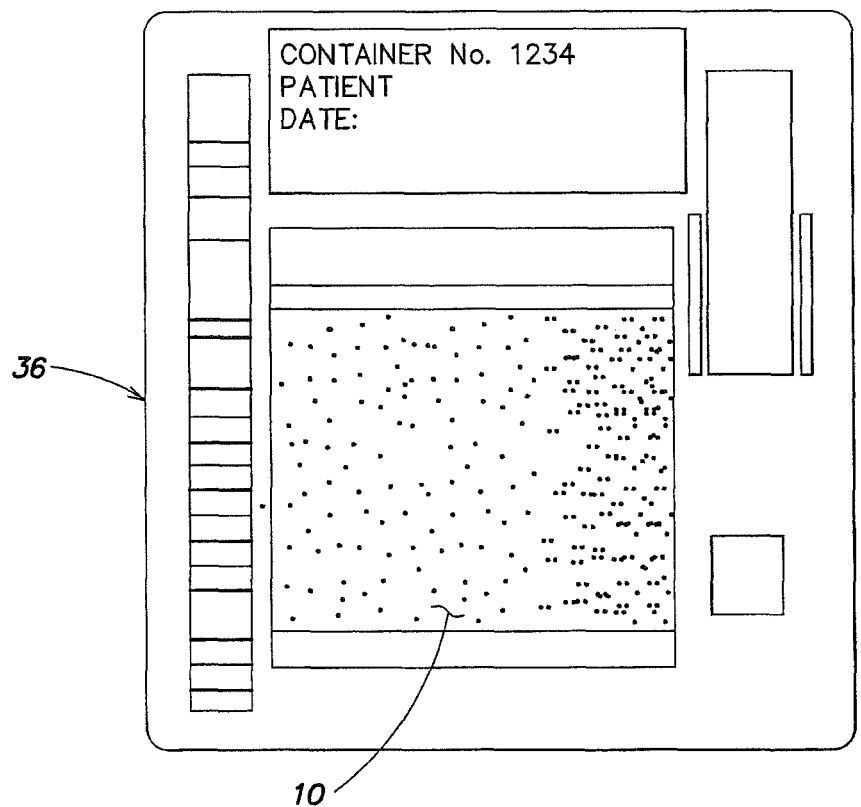
FIG. 6 is a diagrammatic planar view of a disposable container having an analysis chamber.
Figure 7:
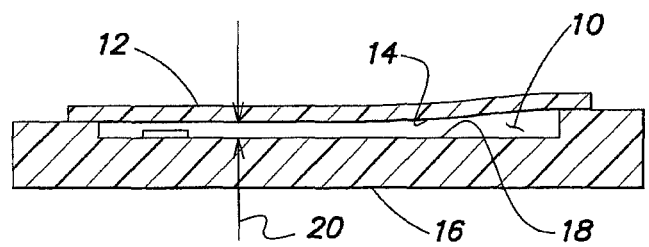
FIG. 7 is a diagrammatic cross-sectional view of a disposable container having an analysis chamber.

Another example of an acceptable chamber 10 is disposed in a disposable container 36 as shown in FIGS. 6 and 7. The chamber 10 is formed between a first panel 12 and a second panel 16. Both the first panel 12 and the second panel 16 are transparent to allow light to pass through the chamber 10. At least a portion of the first panel 12 and the second panel 16 are parallel with one another, and within that portion the interior surfaces 14, 18 are separated from one another by a height 20. This chamber 10 embodiment is described in greater detail in U.S. Pat. No. 6,723,290, which patent is hereby incorporated by reference in its entirety. The analysis chambers shown in FIGS. 2-7, represent chambers that are acceptable for use in the present method. The present method is not, however, limited to these particular embodiments.

An acceptable chamber height is one wherein at least some of the RBCs within the sample individually contact both interior surfaces of the chamber panels, and/or one or more RBC aggregates contact both interior surfaces of the chamber panels, and one or more areas void of RBCs (e.g., lacunae) within the quiescent sample extend between the interior surfaces. Because the size of RBCs within a blood sample are a function of the type of blood sample being analyzed (e.g., human, monkey, horse, goat, fish, bird, etc.), the acceptable chamber height will vary depending on the subject being tested. A chamber height of about two to six microns (2-6 μm) is acceptable for individual RBCs for most animal species based on typical RBC sizes and the fact that RBCs can be deformed to some degree (e.g., the partially compressed sphere discussed above). A hematocrit analysis of an animal species having RBCs substantially larger or smaller than human RBCs, can be performed in a chamber respectively having a larger or smaller chamber height, respectively. In addition, a hematocrit analysis utilizing RBC aggregates can have a chamber height that is dictated by the height of the RBC aggregates.

In some applications, an isovolumetric sphering agent (e.g., a zwitterionic detergent or similarly functioning reagent) is admixed with at least a portion of the sample to cause at least some of the RBCs to assume a substantially spherical geometry. A specific example of a sphering agent is Zwittergent® 3-16 detergent, which is a zwitterionic detergent produced by Calibriochem, an entity of EMD Chemicals, Inc. of New Jersey, U.S.A. The amount of sphering agent added to the sample is an amount adequate to sphere at least a number of RBCs required to perform the present hematocrit analysis. The specific amount will depend on the particular agent and test circumstances, which can be determined by a person of skill in the art without undue experimentation. RBCs in their natural form are often bioconcave disc shaped 38 (see FIG. 1) rather than spherically shaped 40. As a result, absent the effect of the isovolumetric sphering agent, some percentage of the disc shaped RBCs will not contact both of the chamber panels. Increasing the number of RBCs that have a substantially spherical geometry will increase the number of RBCs in contact with both panels, including some 42 that are restrained by the chamber panels, but would otherwise be spherical.

The analysis of the sample quiescently disposed within the chamber is performed using an analysis device that is operable to image at least a portion of the sample and perform an analysis on the image. The image is produced in a manner that permits the optical density of sample to be determined on a per unit basis. The term "per unit basis" or "image unit" means a defined incremental unit of which the image of the sample can be dissected. A pixel, which is generally defined as the smallest element of an image that can be individually processed within a particular imaging system, is an example of an image unit, and an image unit may also include a small number of pixels in a collective unit. The present method is not, however, limited to use with any particular analysis device.

Figure 8:
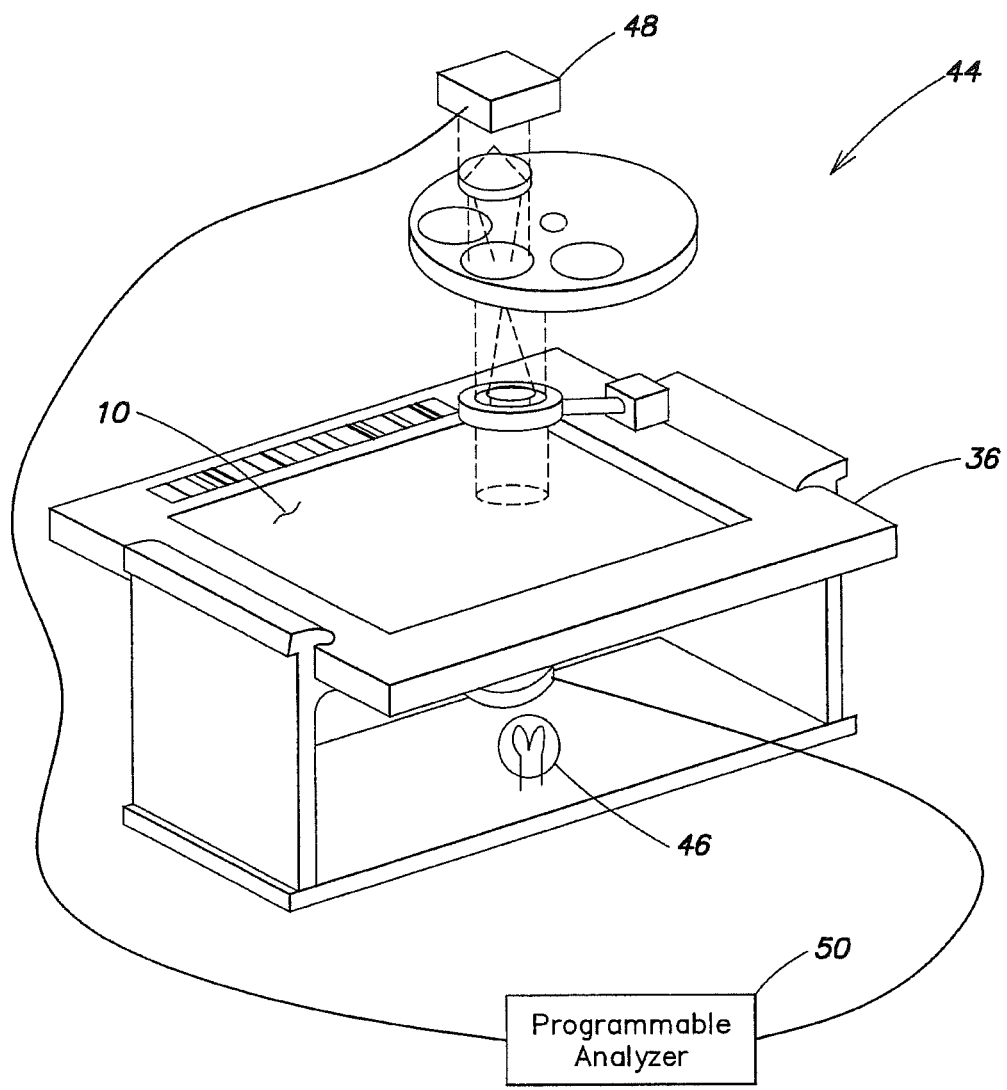
FIG. 8 is a diagrammatic schematic of an analysis device that may be used with the present method.

Now referring to FIG. 8, an example of an analysis device 44 that can be adapted for use with the present method includes a sample illuminator 46, an image dissector 48, and a programmable analyzer 50. The sample illuminator 46 includes a light source that selectively produces light throughout a wavelength range broad enough to be useful for the hematocrit analysis (e.g., approximately 400-670 nm; light at about 413 nm and about 540 nm is particularly effective in determining the optical density (OD) of the RBCs within a sample of human blood), and typically includes optics for manipulating the light. The sample illuminator 46 utilizes transmittance to produce an image. The light transmission properties of the sample can be measured, for example, by positioning a light source on one side of the sample residing within the chamber 10, directing the light through the sample quiescently disposed between chamber panels, and thereafter capturing the light using the image dissector. An example of an acceptable image dissector 48 is a charge couple device (CCD) type image sensor that converts an image of the light passing through the sample into an electronic data format. Complementary metal oxide semiconductor ("CMOS") type image sensors are another example of an image sensor that can be used, and the present invention is not limited to either of these examples. The programmable analyzer 50 includes a central processing unit (CPU) and is connected to the sample illuminator 46 and image dissector 48. The CPU is adapted (e.g., programmed) to selectively perform the functions necessary to perform the present method. It should be noted that the functionality of programmable analyzer 50 may be implemented using hardware, software, firmware, or a combination thereof. A person skilled in the art would be able to program the processing unit to perform the functionality described herein without undue experimentation. U.S. Pat. No. 6,866,823 entitled "Apparatus for Analyzing Biologic Fluids" and issued Aug. 15, 2005, which is hereby incorporated by reference in its entirety, discloses such an analysis device 44.

The analysis device is adapted to determine an OD value associated with the detected light signal on a per unit basis for an imaged portion of the sample. The detected light signal (i.e., the OD values) can be used by an edge finding algorithm to identify the locations and boundaries of RBCs. RBCs that contact both interior surfaces of the chamber have an OD profile similar to that of a partially compressed sphere. The lateral edges of the cell that are not in contact with the surfaces will have an OD that (in relative terms) can be considered to approach zero. The value of the determined OD: 1) increases traveling in a direction toward the center of the RBC (e.g., as the light transmission path through the cell increases); 2) reaches a maximal value and remains substantially constant where the RBC is in contact with the top and bottom surfaces (i.e., when the transmission light path through the RBC is constant); and 3) decreases traveling in a direction away from the center of the RBC (e.g., as the light transmission path through the cell decreases). This characterization of the OD profile of a RBC is particularly uniform for RBCs that are spherically shaped.

The analysis device is further adapted to determine a mean maximal OD value for a group of RBCs and/or RBC aggregates 23 in contact with both interior surfaces. The determination of what constitutes an acceptable group size of RBCs and/or RBC aggregates in contact with the interior surfaces may be done on a per sample analysis basis, or it may be done periodically for "n" number of sample analyses of the same type; e.g., human blood samples. For example, a group of RBCs identified as being in contact with the both interior surfaces can be comparatively evaluated to determine the mean maximal OD and the statistical deviation of the OD within the group. It is desirable to determine the mean maximal OD because the OD of hemoglobin within the cells can vary from cell to cell even within a particular sample. If the standard deviation is greater than a predetermined threshold, a new group of RBCs in contact with both panels can be selected, or the existing group can be expanded, until the aforesaid analysis establishes a group of RBCs having a mean maximal OD with an acceptable standard deviation there from. A mean maximal OD of the RBCs within a group that is about plus or minus one percent (1%) of the mean maximal OD of all the RBCs that contact both surfaces within the sample would, for example, be within acceptable standard deviation values. What constitutes an acceptable standard deviation value can, however, vary depending upon the application at hand and upon the specific statistical analysis being used (e.g., standard error, etc.). Existing statistical data relating to the OD of RBCs is available and can be used in the determination of acceptable OD statistical values. The determination of whether the RBCs within a particular group have a mean maximal OD that is within a clinically acceptable standard deviation can also be adaptive since, as indicated above, it is well known that the population of RBCs within an individual typically have small variations in concentration of hemoglobin and a running standard deviation of the result can be used to determine how many cells must be examined before a mean of acceptable accuracy is obtained; e.g., for samples from a subject having normal blood characteristics, an acceptable group size can be as few as 100 RBCs, whereas samples from a subject having abnormal blood characteristics may require the analysis of 1000 or more RBCs. The specific number of RBCs and/or RBC aggregates in contact with both interior surfaces that are used to establish an acceptable mean maximal OD is not limited to any particular number or percentage of the RBCs within a sample, and may include all (e.g., thousands) of the RBCs in contact with both surfaces.

Figure 9:
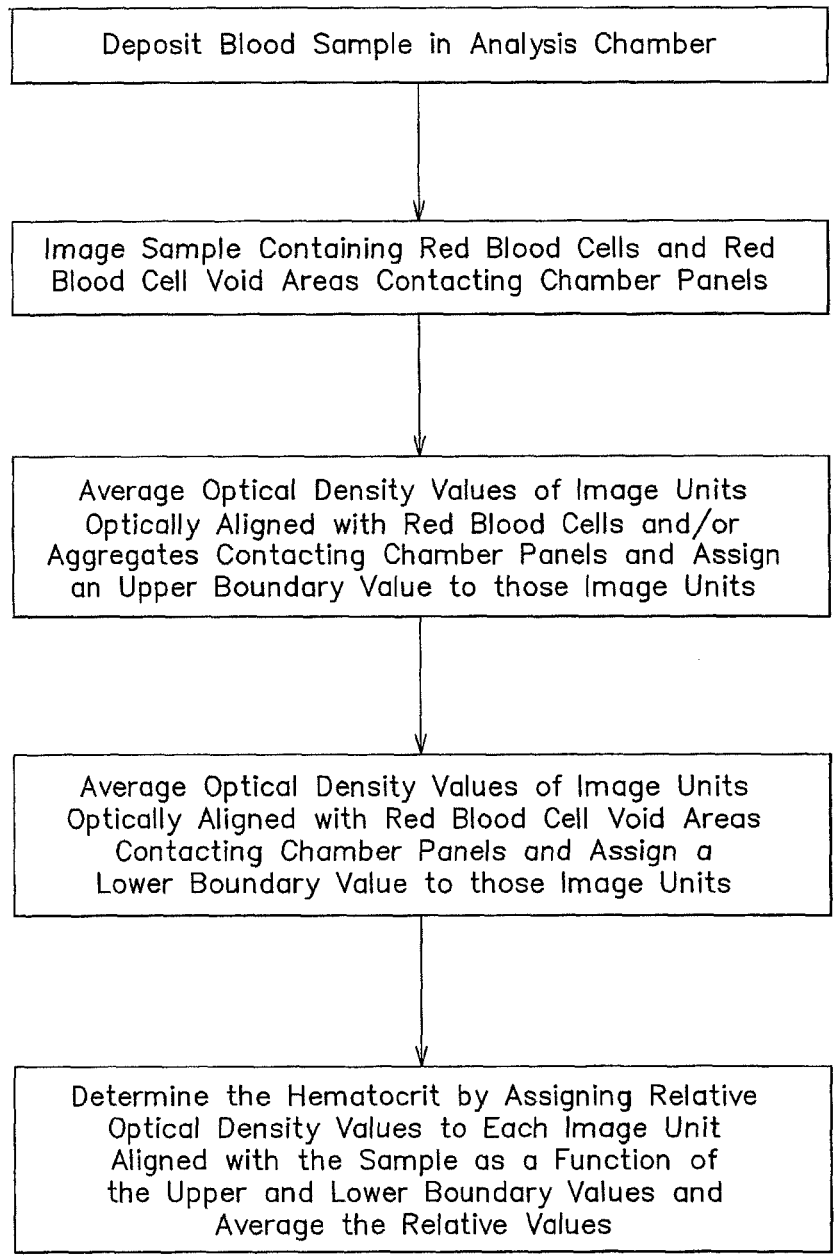
FIG. 9 is a block diagram illustrating a method according to the present invention.

Under a method for determining the hematocrit of a biologic sample according to the present invention, the steps of which method are shown within the block diagram of FIG. 9, a sample of substantially undiluted whole blood is placed in a chamber as is described above. An anticoagulating agent, and in some instances an isovolumetric sphering agent and/or an aggregating agent, is mixed with the sample either prior to its introduction into the chamber or upon introduction into the chamber. Reagents added in dry or semi-dry form, for example via surface coating, are particularly easy to use. The present invention is not limited to dry form reagents, however, and can for example use liquid reagents that do not meaningfully dilute the sample. The sample quiescently resides within the chamber. Under certain circumstances (e.g., very rapid analysis), it may not be necessary to add the anticoagulating agent, but it is preferable to do so in most cases to ensure the sample is in a form acceptable for analysis.

At least a portion of the sample quiescently residing within the chamber is imaged using the analysis device by transmitting light through the sample and detecting the transmitted light. The imaged sample portion includes a number of RBCs and/or RBC aggregates contacting the interior surface of each chamber panel, and at least one area of sample void of any RBCs (RBC void area), extending between the interior surfaces of the chamber panels. Although it is not a requirement that the entire sample residing within the chamber be imaged, it is preferable since doing so typically provides a more complete analysis of the sample (and all of its constituents) and a concomitant increase in accuracy since the distribution of RBCs and lacunae within a chamber is typically non-homogeneous for a sample of substantially undiluted whole blood.

A group of individual RBCs or RBC aggregates in contact with the interior surfaces is determined by the analyzer using the image of the sample portion, and a mean maximal OD having an acceptable standard deviation is determined from that group. As indicated above, the size of the group can vary depending upon the analysis, and may include iterations to determine the aforesaid mean maximal OD having an acceptable standard deviation. An arbitrary upper boundary value of one hundred percent (100%) is assigned to the determined mean maximal OD value of the individual RBCs and/or RBC aggregates in contact with the interior surfaces.

In similar fashion, the analysis device is adapted to identify where one or more RBC void areas (e.g., lacunae) extending between both chamber interior surfaces reside within the chamber. The OD value of the RBC void area(s) is determined, or if more than one RBC void area is present and analyzed, the average of the ODs of the RBC void areas may be determined. An arbitrary lower boundary value of zero percent (0%) is assigned to the OD value of the RBC void area(s).

The hematocrit of the sample is determined by assigning a relative value to the OD value of each unit of the imaged sample portion as a function of the upper and lower boundary values (i.e., as a function of those regions where a RBC extends completely across the height of the chamber, and those regions where there are no RBCs). An average of the percent relative values for each unit is determined. The average relative value is a percentage of the RBC volume of sample between 100% (i.e., all RBCs) and 0% (no RBCs). The percentage is by definition equal to the hematocrit of the sample; i.e., the packed red blood cell volume of the sample.

An advantage of the present method is that it is not necessary to have all of the RBCs within the sample contact each chamber panel. The method can be performed with only some of the RBCs and/or RBC aggregates in contact with both interior surfaces of the chamber. Smaller RBCs and RBC fragments are not used to calibrate the analysis, but are measured for their contribution to the hematocrit. In addition, under the present method the hematocrit of the sample can be determined without knowledge of the total area or volume of the sample within the chamber. Hence, there is no need to use a chamber having a precisely defined height making the manufacture of chambers less expensive.

Although this invention has been shown and described with respect to the detailed embodiments thereof, it will be understood by those skilled in the art that various changes in form and detail may be made without departing from the spirit and scope of the invention. For example, the invention is described above in terms of determining the hematocrit for a sample of substantially undiluted blood. Indeed, one of the advantages of the present invention is its ability to analyze blood without the need for diluents. That said, in alternative embodiments the present invention can be used on blood that has been diluted for various reasons provided the dilution factor of the sample is known or is determinable.

What is claimed is:

1. A method for determining the hematocrit of a blood sample disposed within an analysis chamber, the chamber defined by an interior surface of a first panel, and an interior surface of a second panel, the method comprising the steps of:
    imaging at least a portion of the sample, which sample portion contains one or more red blood cells contacting both of the interior surfaces of the panels and one or more areas void of red blood cells, on a per image unit basis;
    determining a representative optical density value for a plurality of image units optically aligned with portions of the one or more red blood cells, and assigning a first boundary value to the representative optical density value of those image units;
    determining a representative optical density value of a plurality of image units optically aligned with the one or more regions of the sample devoid of red blood cells, and assigning a second boundary value to the representative optical density values of those image units; and
    determining the hematocrit of the sample, which determining includes assigning relative optical density values to image units of the imaged sample portion as a function of the first and second boundary values.

2. An apparatus for determining the hematocrit of a blood sample residing within an analysis chamber defined by an interior surface of a first panel, and an interior surface of a second panel, the apparatus comprising:
    an imaging unit that is operable to image at least a portion of the sample residing within the chamber, which portion contains one or more first sample regions containing one or more red blood cells and one or more second sample regions devoid of red blood cells, and to produce image signals representative of such imaged sample portion; and
    a programmable analyzer operable to determine, using the image signals, optical density values of the imaged portion of the sample on a per image unit basis, and to determine a representative optical density value of image units optically aligned with first sample regions, and to determine a first boundary value based on the representative optical density value of those image units, and to determine a representative optical density value of image units optically aligned with the one or more second sample regions and to determine a second boundary value based on the representative optical density value of those image units, and to determine the hematocrit of the sample based on relative optical density values assigned to the image units of the imaged sample portion as a function of the first and second boundary values.

3. A method for determining the hematocrit of a blood sample disposed within an analysis chamber, the method comprising the steps of:

imaging at least a portion of the sample, which sample portion contains one or more red blood cells, on a per image unit basis, which imaging is performed using one or more wavelengths of light that substantially coincide with an absorption peak for hemoglobin;

determining a representative optical density value for a plurality of image units optically aligned with portions of the one or more red blood cells at the one or more wavelengths of light that substantially coincide with an absorption peak for hemoglobin; and determining the hematocrit of the sample using the representative optical density value determined at the one or more wavelengths of light that substantially coincide with an absorption peak for hemoglobin.

* * * * *